(12) United States Patent
Croom et al.

(10) Patent No.: US 11,534,389 B2
(45) Date of Patent: Dec. 27, 2022

(54) BIO-BASED AND BIODEGRADABLE ELASTOMER FOR COSMETIC AND PERSONAL CARE

(71) Applicant: Grant Industries, Inc., Elmwood Park, NJ (US)

(72) Inventors: Anna K. Croom, Brooklyn, NY (US); Ronald V. Lerum, Leonia, NJ (US); John Gormley, Midland Park, NJ (US)

(73) Assignee: GRANT INDUSTRIES, INC, Elmwood Park, NJ (US)

( * ) Notice: Subject to any disclaimer, the term of this patent is extended or adjusted under 35 U.S.C. 154(b) by 20 days.

(21) Appl. No.: 16/992,831

(22) Filed: Aug. 13, 2020

(65) Prior Publication Data
US 2021/0059924 A1    Mar. 4, 2021

Related U.S. Application Data (60) Provisional application No. 62/976,015, filed on Feb. 13, 2020, provisional application No. 62/893,968, filed on Aug. 30, 2019.

(51) Int. Cl.
| | |
|---|---|
| *A61K 8/02* | (2006.01) |
| *A61K 8/06* | (2006.01) |
| *A61K 8/19* | (2006.01) |
| *A61K 8/87* | (2006.01) |
| *A61K 8/04* | (2006.01) |
| *A61Q 19/00* | (2006.01) |
| *A61Q 17/04* | (2006.01) |

(52) U.S. Cl.
CPC ............. *A61K 8/87* (2013.01); *A61K 8/042* (2013.01); *A61Q 17/04* (2013.01); *A61Q 19/008* (2013.01); *A61K 2800/10* (2013.01); *A61K 2800/54* (2013.01)

(58) Field of Classification Search
None
See application file for complete search history.

(56) References Cited

U.S. PATENT DOCUMENTS

| | | | |
|---|---|---|---|
| 4,661,099 | A | 4/1987 | Von Bittera et al. |
| 5,284,897 | A | 2/1994 | Columbus et al. |
| 8,222,363 | B2 | 7/2012 | Lin et al. |
| 9,376,404 | B2 | 6/2016 | Nakagawa et al. |
| 9,610,237 | B2 | 4/2017 | Burgo et al. |
| 10,035,871 | B2 | 7/2018 | Langer et al. |
| 2003/0092932 | A1 | 5/2003 | Tong et al. |
| 2009/0232752 | A1 | 9/2009 | Carson et al. |
| 2011/0014139 | A1 | 1/2011 | Mala et al. |
| 2011/0045983 | A1 | 2/2011 | Healy et al. |
| 2012/0046358 | A1 | 2/2012 | Cheng et al. |
| 2013/0079486 | A1 | 3/2013 | Hidesaki et al. |
| 2015/0128335 | A1 | 5/2015 | Dehni |
| 2016/0067153 | A1* | 3/2016 | Chen ...................... A61K 8/416 424/70.28 |
| 2018/0079852 | A1 | 3/2018 | Hecking et al. |
| 2018/0208720 | A1 | 7/2018 | Hasegawa et al. |
| 2018/0311140 | A1* | 11/2018 | Perner ........................ A61K 8/44 |
| 2018/0369125 | A1* | 12/2018 | Woodland ................ A61K 8/89 |
| 2018/0371149 | A1 | 12/2018 | Langer et al. |
| 2019/0169390 | A1 | 6/2019 | Peterson et al. |

FOREIGN PATENT DOCUMENTS

| | | |
|---|---|---|
| EP | 1142959 A1 | 10/2001 |
| JP | 3631542 B2 | 3/2005 |
| JP | 6892253 B2 | 6/2021 |
| WO | 2013074655 A1 | 5/2013 |
| WO | 2014167518 A1 | 10/2014 |
| WO | 2018183440 A1 | 10/2018 |
| WO | 2021007489 A1 | 1/2021 |
| WO | 2021231527 A1 | 11/2021 |
| WO | 2021257937 A1 | 12/2021 |

OTHER PUBLICATIONS

Becker et al., "Safety Assessment of Polyurethanes as Used in Cosmetics," 2017, pp. 1-96. (Year: 2017).*
International Search Report and Written Opinion for International Application No. PCT/US2020/046170 (10 Pages) (dated Nov. 18, 2020).
International Preliminary Report on Patentability for International Application No. PCT/US2020/046170 (9 Pages) (dated Mar. 10, 2022).
Written Opinion corresponding to PCT/US2020/041540 (14 Pages) (dated Oct. 16, 2020).

\* cited by examiner

*Primary Examiner* — Brian Gulledge
(74) *Attorney, Agent, or Firm* — Lucas & Mercanti, LLP (57) ABSTRACT

A polyurethane elastomeric rubber composition containing a bio-based polyol cross-linked with a bio-based isocyanate using a urethanation catalyst such as a bismuth catalyst in the presence of a cosmetic emollient is disclosed. The cross-linked polyurethane elastomer rubber is in further aspect of the invention included in a gel after being milled in the presence of a bio-based emollient or mixture of bio-based emollients. The polyurethane elastomeric gel has good compatibility with cosmetic and natural oils and can be used as a gelling agent for these oils among other desirable cosmetic formulary roles.

9 Claims, 1 Drawing Sheet

BIO-BASED AND BIODEGRADABLE ELASTOMER FOR COSMETIC AND PERSONAL CARE

CROSS-REFERENCE TO RELATED APPLICATIONS

This application claims the benefit of priority from U.S. Provisional Patent Application Ser. No. 62/893,968 filed Aug. 30, 2019 and U.S. Provisional Patent Application Ser. No. 62/976,015 filed Feb. 13, 2020, the contents of each of which are incorporated herein by reference.

FIELD OF THE INVENTION

This invention includes compositions and processing/method for preparing polyester and polyurethane type feedstocks for use in cosmetics. The compositions include elastomer systems based on greater than 85% or higher renewable, bio-based feedstocks, which are inherently biodegradable. The compositions can be incorporated into gels and are capable of forming stable mixtures in medium chain esters and less polar hydrocarbons.

BACKGROUND

Silicone elastomers are a broad class of three dimensional cross-linked dimethicone polymers that form three-dimensional polymeric structures and provide a beneficial texture and appearance to cosmetics. They are generally formulated into products to enhance consumer appeal by yielding a preferred sensory aesthetic profile, while functioning as that of a line filler or soft focus particle. Additionally, they can act as sebum absorbers to reduce excess oil on the surface of the skin and act as mattifying agents, which is defined as making the skin less shiny. Further, these cross-linked dimethicone polymers are capable of delivering actives by acting as controlled release polymers and can also reduce the oily texture of high oil content formulas. Silicone elastomers may be co-formulated with common ingredients such as sun protection actives and pigments in order to provide elegant daily wear for skincare and cosmetics. Silicone elastomers are quite safe ingredients but suffer from the perception of being synthetic in origin and not being readily biodegradable, even though they are degradable in the environment.

Polyesters can be synthetic or naturally derived and can vary from rigid thermoplastic solids to low-viscosity oils. From Spiratex literature, Thermoplastic Polyester Elastomers, or TPE, combine the properties of high-performance elastomers and flexible polymers. Sometimes referred to as thermoplastic rubbers, these are high strength materials known for their ability to take repeated flex cycles and their resistance to many chemicals and oils. An important parameter in the characterization of elastomers is measurement of hardness and resilience There are different methods of measuring hardness or stiffness and resilience, i.e. Durometer Hardness as described by ASTM D-2240. The test method describes twelve types of rubber hardness measurement devices known as durometers: Types A, B, C, D, DO, E, M, O, OO, OOO, OOO-S, and R. It is necessary to be within proper scale and adapt based on the behavior of the material. While elastomeric polymers have varying hardness, it was found that the hardness of the present invention was consistent to gel-like materials. The ASTM D2240 is an empirical test method and has been modified and adapted as it is a commonly used procedure for evaluating soft gels, i.e. biopolymer gelatins composed of polypeptides. Briefly, the method uses a texture analyzer to evaluate both hardness and elasticity (resilience) of the present invention and is based on the compression and decompression force profiles of an indenter into a specified depth into the present invention.

Silicone elastomers as generally used in cosmetics are micronized particles (from about 1-100 microns) of silicone rubber, dispersed and semi-swollen into a carrier phase like isododecane, cyclomethicone or light silicone oils. Silicone elastomers for cosmetics require extensive milling and diluting into a carrier phase to obtain the correct balance of cosmetically acceptable properties. In this highly processed form, when the refractive index is matched between the silicone elastomer and the carrier phase, the final mixture can give the appearance of a gelled homogenous system, only further revealing the presence of the elastomer in sensorial testing. For instance, if the carrier phase is volatile, the act of spreading the silicone elastomer mixture on the skin results in the carrier phase vaporizing and leaving a micronized "ball bearing" particle of elastomer on the skin that exhibits a desirable texture and provides a mattifying property for sebum absorption on the skin. The state of the art of silicone elastomer dispersions as used in cosmetics includes almost all premium leave-on skin care product forms that yield a texture and function exceedingly well regarded by formulators and consumers alike.

While performance of dispersed silicone elastomers is unparalleled, there is a demand for alternatives to silicone elastomers since silicones, in part, come from non-renewable feedstocks of petroleum origin. Therefore, a primary goal is to create a high performing dispersed elastomer based primarily on feedstocks of renewable bio-sourced origins. Secondly, while they can be chemically degraded in the environment over time, silicones are not inherently biodegradable by microbial action. Therefore, a second criteria is an inherently biodegradable elastomer dispersion. Thirdly, the inherent nature of silicone elastomers exhibits functional compatibility with branched chain hydrocarbons like isododecane and good compatibility with silicone fluids. They are therefore medium polar, semi-hydrophobic in nature and as a consequence will phase separate from more polar esters without the addition of other compatibilizing ingredients or emulsifiers. Therefore, an additional goal is to create a dispersed gelling or thickening high performing elastomer that meets the first two criteria but also providing compatibility with more polar cosmetic ingredients, such as esters and medium chain triglycerides (MCT), in order to formulate with ingredients not directly attainable with silicone elastomers. Fourth, the alternative to silicone gel should have comparable sensory aesthetic profiles.

Options for alternatives to petroleum-based polymers are of increasing importance for application in the personal care industry. Bio-based and biodegradable elastomeric polymers are an essential class of materials for the enhancement of textural attributes in cosmetic compositions. Elastomeric polymers swollen and dispersed in various cosmetic fluids may provide new formulation opportunities that are not achieved with current elastomeric polymers, i.e. hydrogels, silicone gels, oil-based thickeners, etc. Consequently, there is a need to develop new elastomeric polymers with enhanced textural attributes similar to those of silicone gels, hydrogels, oil-based thickeners, etc. The bio-based and biodegradable gel presented in this invention has good compatibility with cosmetic and natural oils and can be used as a gelling agent for these oils.

Prior art related to the leave on cosmetic industry includes numerous classes of polyesters and polyurethanes performing a variety of functions. Thousands of polyesters and polyurethanes are listed for commerce in the COSING (EU public cosmetic ingredients database). Many of these ingredients are common fully synthetically manufactured film forming polymers that act as hair sprays or binders when combined with other solvents, including water. Often these are dispersed as lattices or dispersions in water, often made from prepolymers that are crosslinked with di- or tri-amino chain extenders to form carbamates. Amine-based building blocks are not desirable for cosmetic raw material development due to the prevalence of high odor profiles and the common phenomenon of yellowing the final product formulation. Another class of urethanes are sold as solid, predominantly non-swellable micronized powders based on synthetic feedstocks from petroleum sources. For example, Grant Industries sells Granpowder USQ, a product containing 30-40% of a micronized non-swellable urethane powder with the INCI name HDI/Trimethylol Hexyllactone Crosspolymer. While exhibiting excellent tactile and soft focus (optical) properties, it does not have elastic properties analogous to silicone elastomers. It is a free-flowing powder with little to no elastic properties when dispersed in medium polar carrier fluids like MCTs.

SUMMARY OF THE INVENTION

In view of the foregoing, the invention includes a bio-based and biodegradable swellable, elastic non-ionic, non-aqueous material using a polyester linked between a multi-functional, e.g. a tri-functional, polyurethane crosslinker in a natural origin reaction solvent, which is also referred to herein as a cosmetic emollient, using a urethanation catalyst such as a bismuth catalyst. The preferred catalysts are generally considered to be those which are non-toxic/safe alternatives to amine-based, organo-mercury or organo-tin based urethane catalysts. This solvent class can include MCT.

The invention also includes a process for preparing a gel. The process includes a milling process of the MCT based rubber elastomer with simultaneous or subsequent diluting with a solvent, which can be the same or different from the reaction solvent. A volatile cosmetic alkane of renewable feedstock is preferred to achieve a desired sensory aesthetic profile.

In one aspect of the invention there are provided cross-linked polyurethane elastomer rubber compositions which include
  (a) a cross-linked polyurethane elastomer rubber;
  (b) a cosmetic emollient; and
  (c) a urethanation catalyst,
wherein the cosmetic emollient forms a solvent matrix which substantially surrounds the cross-linked polyurethane elastomer rubber. For purposes of the present invention, "substantially surrounds" shall be understood to mean that the solvent matrix is in intimate contact on the surface of the rubber and covers a substantial portion of the rubber surface. The emollient may but does not always completely envelop the rubber.

In another aspect of the invention there are provided processes for preparing the cross-linked polyurethane elastomer rubber compositions described herein. The processes include reacting a polyisocyanate with a prepolymer having at least two free hydroxyl groups in the presence of a urethanation catalyst and a cosmetic emollient under conditions sufficient to form a cross-linked polyurethane rubber.

Further aspects of the invention include gel compositions which contain a mixture of a cross-linked polyurethane elastomer rubber composition as described herein, in a milled form and at least one cosmetic emollient as well as methods of making the gel compositions. The said gel composition is a rubber dispersion, refined via one or more milling and diluting steps whereby each step yields a targeted equilibrium particle size range leading to a final product in the 1 to 100 micron range, preferable 1 to 60 microns. Still further aspects of the invention include cosmetics, emulsions, lotions, creams, etc., and products which contain the inventive compositions and gels.

As a result of the invention, there is provided a silicone alternative elastomeric gel of at least 85 or even >98% bio-based material. This bio-based elastomer was submitted to testing that resulted in achieving "Ultimate Biodegradable/Inherent Biodegradable" and is unknown in the prior art in relation to the body of performance attributes otherwise achieved. The main invention is an elastomer that is not silicone-based but approaches the high value texture previously only achievable via silicone chemistry. The invention disclosed is trademarked as Gransense™ and will be commercially available as a cosmetic material from Grant Industries (Elmwood Park, N.J., USA).

DETAILED DESCRIPTION OF THE INVENTION

In one aspect, the present invention relates to a polyurethane elastomeric rubber composition which comprises a bio-based polyol cross-linked with a bio-based isocyanate using a urethanation catalyst such as a bismuth catalyst in the presence of a cosmetic emollient. Isocyanates are compounds containing the isocyanate group (—NCO). They react with compounds containing alcohol (hydroxyl) groups to produce polyurethane polymers. The cross-linked polyurethane elastomer rubber is in further aspect of the invention included in a gel after being milled in the presence of a bio-based emollient or mixture of bio-based emollients. The polyurethane elastomeric gel has good compatibility with cosmetic and natural oils and can be used as a gelling agent for these oils among other desirable cosmetic formulary roles. The increased polarity of the polyurethane elastomer gel versus silicone elastomer counterparts allows for its incorporation into increasingly polar formulation media in which silicone elastomers would otherwise not be compatible.

The cross-linked polyurethane elastomer rubber compositions of the invention preferably are those in which the prepolymer, the polyisocyanate, and the cosmetic emollient are bio-based and biodegradable. In some preferred aspects of the invention, the cross-linked polyurethane elastomer rubber composition is comprised of greater than about 85%, preferably greater than about 95% and in some alternative embodiments, greater than about 99% renewable, bio-based feedstocks or, stated alternatively, plant-derived (non-petroleum based) feedstocks. In an alternative embodiment, the rubber composition can be made using a polyester prepolymer which is derived from entirely synthetic or petroleum-based feedstocks rather than bio-based feedstocks. Similarly, the emollient or mixture of emollients and/or the isocyanate can, in alternative embodiments, be derived from synthetic or petroleum based feedstocks rather than bio-based feedstocks.

Through a milling and dilution process, the polyurethane rubber composition is converted into an elastomeric gel that provides a smooth, non-tacky, non-oily, moisturizing skin-feel with enhanced playtime on the skin. The elastomeric gel of this invention is an elegant addition to the cosmetic formulator's toolbox for creating stable cosmetic formulas with improved compatibility toward more polar cosmetic emollients, actives, and additives that are commonly incorporated into the oil phase of oil-based cosmetics.

In this invention, a generalized process for preparing the polyurethane rubber composition and its subsequent conversion to a polyurethane elastomeric gel follows these steps: First, a bio-based prepolymer is reacted with a bio-based isocyanate using a urethanation catalyst such as a bismuth catalyst at a suitable, controlled temperature, e.g. from about 20° C. to about 100° C. in a reaction medium of bio-based emollient or a mixture of bio-based emollients which act as solvent(s) to form an elastomeric polyurethane rubber composition. Alternatively, the process can include forming the rubber composition without stirring at room temperature over about 24 hours.

As a result of the reaction conditions, the emollient forms a solvent matrix which substantially surrounds and/or swells the polyurethane rubber.

Second, the formed rubber is converted to a dispersion via high shear milling whereby an optional additional charge of the same or different bio-based emollient is added to the rubber composition before or after milling. The mixture is preferably milled into a polyurethane gel concentrate, using a suitable device known to those of ordinary skill, for example, a high-shear disperser mixer. The milling preferably reduces the particle size of the rubber composition to preferably less than about 100 microns, and more preferably to a range of from about 1 to about 60 microns in cross-sectional diameter.

Third, the elastomer concentrate is finished to a cosmetically appropriate viscosity by further dilution with a secondary solvent which can be a bio-based emollient having either volatile or non-volatile properties depending on the targeted application and desired skin-feel properties of the finished elastomer gel. Thus, the gels may include a bio-based emollient or mixture of emollients which enhances aesthetic skin feel and/or enhance cosmetic formulation compatibility.

In some aspects, the rubber composition is comprised of a pre-polymer, in amounts of from about 5 to about 25 weight percent. The pre-polymer contains at least 2 hydroxyl groups. The preferably bio-based isocyanate can be present in amounts of from about 1 to about 20 weight percent and optionally the isocyanate contains from about 15 to about 38% or, alternatively, from about 15 to about 28% —NCO group. The overall molar ratio of —NCO of the isocyanate to —OH of the polyol can be from about 2:1 to about 1:2. The polyol can optionally have a hydroxyl value between 50-200, or alternatively 90-200 mg KOH/g.

The rubber composition also can include from about 0.1 to about 2.5 weight percent of the catalyst.

Other preferred aspects of the inventive rubber include that it has a hardness force greater than 200 g or, alternatively greater than 500 g, and less than 4000 g as measured by a texture analyzer prior to any milling or dilution and that it has a resilience greater than or equal to 70%, or alternatively 90%.

The rubber of the invention can in some aspects be classified as Ultimate Biodegradable/Inherent Biodegradable according to OECD 301-B and it can be made to contain as high as >97.0% Bio-based Carbon in accordance with ASTM D6866-18.

Formation of a millable elastomeric rubber than can be converted into a cosmetically elegant and stable gel requires consideration of several physical parameters inherent to the rubber formation. The hardness of the polyurethane rubber is an important factor that determines if it can be readily processed into a gel. If the polyurethane rubber is too hard, the rubber granules will not swell properly or grind into a smooth gel upon processing with an emollient. On the other hand, if the polyurethane rubber is too soft it will not easily process into a gel due to stickiness and lack of swellable granules. Three important factors determine the hardness of the polyurethane rubber:

First, the ratio of polymer content to carrier fluid is essential to consider to synthesize an optimal polyurethane rubber. The total weight percent of biobased emollients should range between 70-95%, or alternatively between 70-90% in the polyurethane rubber. If too much carrier fluid is used, the density of the elastomeric network will be too low to maintain viscosity. If too little carrier fluid is used, the polymer content may be too dense to properly disperse when milled.

Second, the ratios of bio-based hydroxyl functionality of the bio-based pre-polymer to the NCO functionality of the polyisocyanate can be between 2:1 to 1:2, and preferably 1:1.

Third, the amount of catalyst used in the synthesis of the polyurethane rubber is another factor that determines its ability to be processed into a gel. If too much catalyst is used the rubber will over-cure and will be too hard for processing into a gel. If too little catalyst is used the rubber will not form. In practice, the amount of catalyst can be about 0.1-2.5% by weight.

The gel composition of the invention can have a viscosity ranging from about 15,000 to about 1,000,000 cP in many embodiments of the invention and from about 40,000 to about 1,000,000 cP in alternative embodiments. The gels are optionally those which can be classified as Ultimate Biodegradable/Inherent Biodegradable according to OECD 301-B and/or contain up to 97% Bio-based Carbon in accordance with ASTM D6866-18. Optionally, a finisher containing an alcohol or optionally an amine may be added to quench unreacted isocyanate groups to the compositions of the invention. The gels of the invention can be a non-Newtonian fluid or a thixotropic fluid. The gels of the invention can include an optional personal or healthcare active, such as without limitation a vitamin such as vitamin C, and Vitamin A, sunscreen, plant extract, and/or fragrance.

Definitions

Thixotropic Gel Properties

The preferred polyester and/or polyurethane linkages in the elastomeric gel allow for the ability for hydrogen bonding to form over time. This behavior of the gel allows for a thixotropic property.

A thixotropic fluid displays non-Newtonian pseudoplastic behavioral change as a dependence on time. Under static conditions these types of gels (within the scope of this invention) will appear as a "pseudo-plastic" but will begin to flow and have a reduction in viscosity when a constant force (agitation, mixing, shaking, shear) is applied. When there is no force applied and after a period of time the gel will recover to its initial steady state. Common examples of thixotropic fluids are yogurt and polyvinyl alcohol adhesive glue gel. There are many formulation advantages when incorporating a thixotropic gel into a formula compared to conventional oils, waxes, rubbers, or powders. Examples include but are not limited to maintaining film thickness upon application and improving spreadability of the cosmetic product during application and usage to impart a soft and elegant feel.

Thixotropic gels offer many advantages for formulators, such behaving as a suspending and thickening agent in sprays as well as memory type applications in both skin care and personal care. Additionally, thixotropic materials are considered process aids, and can offer enhanced stability, and controlled spreadability of the personal care product. Compared to silicone elastomers the shear thinning behavior may enhance the ease of mixing when incorporating other ingredients into the formula. The reduced viscosity would require less strain on mixing and shear dispersing processing equipment and a more rapid incorporation of personal care actives, thereby leading to a reduction in cost and timesaving in production. Another benefit of the thixotropic gel is to stabilize the formula and minimize phase separation and potentially stabilize particle suspensions, i.e. pigments.

Ultimate Biodegradability—The level of degradation achieved when the test compound is totally utilized by microorganisms resulting in the production of carbon dioxide, water, and mineral salts, and new microbial cellular constituents (biomass).

Inherent Biodegradability—A classification of chemicals for which there is unequivocal evidence of biodegradation (primary or ultimate) in any test of biodegradability.

Elastic—able to encompass variety and change; flexible and adaptable.

Elastomer—a natural or synthetic polymer/macromolecular material having elastic properties which can return to shape when distorted by physical stress, e.g. rubber.

Polymer—a substance that has a molecular structure consisting chiefly or entirely of a large number of similar units bonded together, e.g., many synthetic organic materials used as plastics and resins; Proteins have polypeptide molecules, which are natural polymers made from various amino acid monomer units. Nucleic acids are huge natural polymers made up of millions of nucleotide units.

Appropriate polymers and prepolymers include but are not limited to:
Azelate Polyols
Butanediol/adipic acid copolymer
Butanediol/azelaic acid copolymer
Butanediol/sebacic acid copolymer
Capryloyl Glycerin/sebacic acid copolymer
Capryloyl glycerin/sebacic acid copolymer
Capryloyl Glycerin/Sebacic Acid Copolymer
Castor oil derived Polyhydroxystearic acid
Cellulose
Collagen
Diheptyl succinate (and) capryloyl glycerin/sebacic acid copolymer
Dilinoleic acid/propanediol copolymer
Dimer acid diol
Lecithin
Poly(polyol sebacate)
Polybutylene succinate
Polycaprolactone
Polyester
Polyethylene Glycol
Polyglycerol
Polyglycolides
Polyhydroxyalkanoates
Polyhydroxybutyrates
Polylactic acid and Polylactides
Polylactide-co-glycolides
Polysaccharides
Propanediol/adipic acid copolymer
Propanediol/azelaic acid copolymer
Propanediol/sebacic acid copolymer
Propylene glycol/adipic acid copolymer
Propylene glycol/azelaic acid copolymer
Propylene glycol/sebacic acid copolymer
Pullulan
Starch
Trimethylpentanediol/adipic acid copolymer, and mixtures thereof.

The preferred polyol for the synthesis of the elastomeric rubber is a diol- or polyol-functionalized polyester with an effective molecular weight between 280-3000 g/mol and alternatively between 500-3,000 g/mol. The polyol should have an acid value <2 (mg KOH/g), a hydroxyl value between 50-200 or 90-200 (mg KOH/g), and water content <0.1 (K.F., w/w %). A preferred prepolymer is dilinoleic acid/propanediol copolymer is derived from 100% bio-based sources and has good compatibility with cosmetic oils. Preferably the copolymer should be terminated in hydroxyl groups and have a low acid value, as hydroxyl groups react more readily with isocyanates than carboxylic acids. Castor oil can also be used as polyol for the synthesis of polyurethane rubbers because it naturally contains multiple hydroxyl groups. In addition, there are many polyols available that can be used in the synthesis of polyurethane elastomer gels.

Appropriate polyols include but are not limited to:
1,2-ethanediol
1,2-propanediol
1,3-propanediol
caprylyl glycol
castor oil
corn oil
diethylene glycol
ethylene glycol
ethylene oxide
glycerol
heptanediols
Hexanediols
hydrogenated or epoxidized vegetable oil
Isomeric butanediols
isosorbide
linseed oil
olive oil
other hydroxy containing compounds
pentaerythritol
Pentanediols
polytetramethylene ether glycol
propylene glycol
propylene oxide
silanol
sugar alcohols
Triethylene glycolether gylcol,
and mixtures thereof.

Appropriate Carboxylic Acids include but are not limited to
Azelaic acid
Citric acid
Dilinoleic acid
Dimer acid
Itaconic Acid
Lactic acid
Polylactic acid
Sebacic acid
Trilinoleic acid,
and mixtures thereof.

The emollients used in the synthesis of the polyurethane rubber can be esters, ethers, alkanes, or mixtures thereof. The emollients used in the processing of this rubber into a gel can be esters, ethers, alkanes, or mixtures thereof. The emollients preferably have a viscosity between 1-65 at 20° C. (mPas). The spreading value (mm$^2$/10 min) of the emollient is preferably between 500-2500.

Appropriate emollients or solvents include but are not limited to:
Butyl Lactate
Butylene glycol
C12-15 Alkyl Lactate
C12-C15 Alkyl benzoate
C13-C15 alkanes
C16-18 alkanes
C18-C22 alkanes
Caprylic/Capric Triglyceride
Caprylic/Capric/Succinic Triglyceride
Caprylyl-Caprylate/Caprate
Castor oil
Cetyl Ethylhexanoate
Coco-Caprylate/Caprate
Cocoglycerides
Decyl oleate
Dibutyl adipate
Dicaprylyl Carbonate
Dicaprylyl Ether
Diheptyl Succinate
Dodecane
Ethyl lactate
Ethylhexyl Isononanoate
Glycerin
Glyceryl trihexanoate
Glyceryl triheptanoate
Glyceryl trioctanoate.
Hemisqualane
Heptyl Undecylenate
Isododecane
Isononyl Isononanoate
Isopropyl Myristate
Isopropyl palmitate
Jojoba oil
Mirystyl Myristate
Neopentyl Glycol Diheptanoate
Octyl palmitate
Oleyl Eurcate
Olive squalane
Polybutene
Propylene carbonate
Propylene glycol
Propylene glycol dicaprylate/dicaprate
Shea butter ethyl esters
Squalane
Tridecane
Triethylhexanoin
Triheptanoin
Undecane,
and mixtures thereof.

A 1,5-pentamethylene diisocyanate trimer was used as the preferred isocyanate for the synthesis of the polyurethane elastomer. This isocyanate, derived from bio-based feedstocks, readily reacts with polyols in the presence of a polyurethane catalyst and emollient to form polyurethane rubbers. In addition, a plethora of di-functional isocyanates are available that are widely utilized in industry.

Appropriate functionalized isocyanates include but are not limited to:
1,1'-Methylenebis(4-isocyanatocyclohexane)
1,3,3-Trimethyl-1-(isocyanatomethyl)-5-isocyanatocyclohexane
1,3,5-Triazine-2,4,6(1H,3H,5H)-trione, 1,3,5-tris[(5-isocyanato-1,3,3-trimethylcyclohexyl)methyl]
1,3-Bis(isocyanatomethyl)cyclohexane
1,3-Diazetidine-2,4-dione, 1,3-bis[4-[(2-isocyanatophenyl)methyl]phenyl]
1,3-Diazetidine-2,4-dione, 1,3-bis[4-[(4-isocyanatophenyl)methyl]phenyl]
1,3-Phenylene diisocyanate
1,3-Propanediol, 2-ethyl-2-(hydroxymethyl)-, reaction products 5-isocyanato-1-(isocyanatomethyl)-1,3,3-trimethylcyclohexane
1,4-Phenylene diisocyanate
1,5-Diisocyanato-2-methylpentane
1,5-Pentamethylene diisocyanate
1,5-Pentamethylene diisocyanate dimer
1,5-Pentamethylene diisocyanate trimer
1,6-Hexamethylene diisocyanate
1,8-Diisocyanato-2,4-dimethyloctane
2,2,4-Trimethylhexane 1,6-diisocyanate
2,2'-Diisocyanatodiphenylmethane
2,4,4-Trimethylhexane 1,6-diisocyanate
2,4,6-triisopropyl-m-phenylene diisocyanate
2,4'-Methylenediphenyl diisocyanate
2,4-Toluene diisocyanate
2,4-Toluene diisocyanate trimer
2,4-Toluenediisocyanate dimer
2,5(6)-Bis(isocyanatomethyl)bicyclo[2.2.1]heptane
2,6-Toluene diisocyanate
3,3'-Dimethoxy-4,4'-biphenylene diisocyanate
3,3'-Dimethyl-4,4'-biphenylene isocyanate
4,4',4"-Triisocyanatotriphenylmethane
4,4-MDI uretidinone
4,4'-Methylenediphenyl diisocyanate
80% 2,4-TDI; 20% 2,6-TDI, blend of isomers
Benzene, 1-[(2,4-diisocyanatophenyl)methyl]-3-isocyanato-2-methyl
Bis(isocyanatomethyl)cyclohexane
Diphenyl oxide 4,4'-diisocyanate
Diphenylmethanediisocyanate
Hexamethylene diisocyanate biuret
Hexamethylene diisocyanate dimer
Hexamethylene diisocyanate isocyanurate
Methyl 2,6-diisocyanatohexanoate
Naphthalene, 1,5-diisocyanato
Octahydro-4,7-methano-1H-indenedimethyl diisocyanate
Polymethylenepolyphenyl polyisocyanate
Tris(4-isocyanatophenyl) thiophosphate,
and mixtures thereof.

Bismuth or zinc based polyurethane catalysts are preferred for the synthesis of the polyurethane rubber due to their relatively low-toxicity. However, organometallic and amine based polyurethane catalysts can also be used. Bismuth based catalysts are preferred for cosmetic applications due to low toxicity relative to amine, mercury, or tin-based catalyst.

Possible urethanation catalysts include but not limited to:
Lead Compounds
Mercury compounds (i.e. mercury salts, mercury hydroxide, mercury decanoate, bis(phenyl mercury) dodecenyl succinate), and Stannous compounds (i.e. stannous octoate, stannous chloride).

Preferred urethanation catalysts with reduced toxicity relative to tin, mercury and lead include but are not limited to:
Acid Phosphate complex
Aluminum
Bis-(2-dimethylaminoethyl)-ether
Bismuth carboxylate
Bismuth esters
Bismuth Citrate
Bismuth alkanoates
Bismuth neodecanoate
Dimethylaminopropylamine
DABCO (1,4-diazabicyclo[2.2.2]octane and DABCO derivative
Metal complex
Mixed carboxylate
N-methylimidazole
N-methylmorpholine
Tertiary amines
Triethylamine
Zinc acetate
Zinc acetylacetonate
Zinc complex
Zinc esters and alkanoates
Zinc neodecanoate
Zinc octoate
Zinc oxalate
Zirconium,
and mixtures thereof.

Cosmetic powders may be combined with the invented elastomer to enhance the performance of the gel by altering its texture, absorbency, formula stability, and soft-focus features desirable in finished cosmetic products. The powders may be used to provide structural support or behave as fillers or alter the final appearance of the gel to have a more "mattifying, soft focus" appearance. The powders can be used to provide a good slip and smoothness to the final formulation of the product, but not limited to, press powders, lotions, creams, hair gels, hair creams, mascaras, body creams, serums, lip care etc. The powders can also be used to modify the viscosity of the final formula due to its inherent nature to absorb a finite amount of liquid from the formula.

Appropriate powders include but are not limited to (synthetic and natural) and blends thereof:
Acrylate copolymer
Alumina
Aluminum Oxide
Aluminum Silicate
Boron Nitride
Butter coated powders (where the Butter can be, but are not limited to, Shea, Mango, Cocoa, Almond, where the powders are but not limited to, Mica, Talc, Aluminum, Cellulose, Polyhydroxyal kanoate)
Calcium Starch Octenylsuccinate
Cellulose
Cellulose Acetate
DimethiconeNinyl dimethicone crosspolymer
Glass beads
Kaolin Clay
Mica
Natural waxes (such as but not limited to, Carnauba Wax, Beeswax, Castor oil etc.)
Nylon
Polybutylene Succinate
Polyester
Polyethylene
Polyhydroxyalkanoate
Polylactic acid
Polymethylsilsequioxane
Polypropylene
Polytetrafluoroethylene
Polyurethane powder (such as the powder of a copolymer of hexamethylene diisocyanate and of trimethylol hexyl lactone)
Polyvinylalcohol
Polyvinylchrloride
Sericite
Silica
Starch
Synthetic waxes
Paraffin wax
Talc
Trimethoxysilicate
Zeolite
Zinc Stearate
Zinc oxide and
Titanium dioxide.

When processing the polyurethane elastomer rubber into a gel, a compatible emollient must be used in order for the newly forming polymeric microparticles to react. Triglycerides, esters, and ethers with high polarity can be used to swell the particles during the reaction and milling process. Preferable emollients include plant origin medium chain triglycerides (MCT) such as glyceryl trihexanoate, glyceryl triheptanoate, and glyceryl trioctanoate, or mixtures thereof. Once the elastomer rubber is processed into a concentrated gel, volatile emollients with a dry skin feel can be added to the gel until the desired viscosity is achieved. Triglycerides, esters, ethers, and alkanes can be used during this process.

The stability of polyurethane elastomer gel is dependent on the emollient or mixture of emollients used in the synthesis of the rubber and the processed gel. If the polarity of the emollient/s is too low, the gel may initially form but will separate over time. Generally, triglycerides, esters, ethers, and alkanes can be used in various combinations. Preferably a mixture of plant origin emollients such as medium chain triglycerides, C9-C12 alkanes, and esters derived from short-chain fatty acids and alcohols such as caprylate/caprate. In some aspects, the emollients can be considered secondary solvents and be selected from among for example, triheptanoin; undecane; tridecane. Alternatively, the secondary solvents are naturally derived alkanes or naturally derived esters.

The gel compositions can include a mixture of the cross-linked polyurethane elastomer compositions described herein, preferably in micronized form and a cosmetic emollient. For example, some gel compositions can include from about 5 to about 30 weight % or from about 5 to about 17 weight % of the micronized cross-linked polyurethane elastomer rubber composition.

The gel compositions can also include one or more cosmetically acceptable ingredients or emollients in amount from about 70 to about 95 weight % or from about 83 to about 95 weight %.

EXAMPLES

In the following examples, we describe a bio-based and biodegradable cross-linked polyurethane elastomer rubber and a bio-based and biodegradable cross-linked polyurethane elastomer gel. The elastomer rubber is processed into the elastomer gel which can be further processed for optimal performance as a cosmetic ingredient.

As outlined in the description of the invention, the formation of a polyurethane rubber involves the cross-linking of a bio-sourced pre-polymer containing at least two hydroxyl groups with a polyisocyanate in the presence of a catalyst and sufficient amounts of bio-based cosmetic emollients. The pre-polymer selected for the examples was a copolymer of C18-unsaturated fatty acid dimers and 1,3-propanediol (DAPD) with a hydroxyl value within the range of 60-80 mg KOH/g and a bio-based aliphatic polyisocyanate, pentylene diisocyanate trimer (PDT) containing around 20% NCO content. The bismuth catalyst was bismuth neodecanoate. The cosmetic emollient was a mixture of coco-caprylate/caprate and glyceryl triheptanoate.

Example 1: Synthesis of Polyurethane Rubber

To an 8 oz glass jar was added 11.25 g (12.5 wt %) DAPD polyol, 3.15 g (3.5 wt %) PDT, 18.81 g (20.9 wt %) of glyceryl triheptanoate and 56.34 g (62.6 wt %) of coco-caprylate/caprate. The mixture was stirred by a propeller mixer for 10 minutes and 0.45 g (0.5 wt %) of a bismuth catalyst was added. After stirring the mixture for an additional 5 minutes, stirring was stopped and the reactor was placed in an oil bath and heated to 60° C. The mixture was heated until a cured rubber is formed whereupon the reactor is removed from heat. Typical gelling times range between 5 minutes and 2 hours.

Example 2: Synthesis of High-Density Polyurethane Rubber

To an 8 oz glass jar was added 17.05 g (18.9 wt %) DAPD polyol, 4.77 g (5.3 wt %) PDT, 16.9 g (18.78 wt %) of glyceryl triheptanoate and 50.6 g (56.2 wt %) of coco-caprylate/caprate. The mixture was stirred by a propeller mixer for 10 minutes and 0.68 g (0.76 wt %) of a bismuth neodecanoate was added. After stirring the mixture for an additional 5 minutes, stirring was stopped and the reactor was placed in an oil bath and heated to 60° C. The mixture was heated until a cured rubber is formed whereupon the reactor is removed from heat. Typical gelling times range between 5 minutes and 2 hours.

Example 3: Synthesis of Low-Density Polyurethane Rubber

To an 8 oz glass jar was added 6.82 g (7.58 wt %) DAPD polyol, 1.91 g (2.12 wt %) PDT, 20.27 g (22.5 wt %) of glyceryl triheptanoate and 60.73 g (67.5 wt %) of coco-caprylate/caprate. The mixture was stirred by a propeller mixer for 10 minutes and 0.27 g (0.3 wt %) of a bismuth neodecanoate. After stirring the mixture for an additional 5 minutes, stirring was stopped and the reactor was placed in an oil bath and heated to 60° C. The mixture was heated until a cured rubber is formed whereupon the reactor is removed from heat. Typical gelling times range between 5 minutes and 2 hours.

Example 4: Synthesis of Polyurethane Rubber in Glyceryl Triheptanoate

To an 8 oz glass jar was added 11.25 g (12.5 wt %) DAPD polyol, 3.15 g (3.5 wt %) PDT, and 75.15 g (83.5 wt %) of glyceryl triheptanoate. The mixture was stirred by a propeller mixer for 10 minutes and 0.45 g (0.5 wt %) of bismuth neodecanoate was added. After stirring the mixture for an additional 5 minutes, stirring was stopped and the reactor was placed in an oil bath and heated to 60° C. The mixture was heated until a cured rubber is formed whereupon the reactor is removed from heat. Typical gelling times range between 5 minutes and 2 hours.

Example 5: Synthesis of Polyurethane Rubber in Coco-Caprylate/Caprate

To an 8 oz glass jar was added 11.25 g (12.5 wt %) DAPD polyol, 3.15 g (3.5 wt %) PDT, and 75.15 g (83.5 wt %) of coco-caprylate/caprate. The mixture was stirred by a propeller mixer for 10 minutes and 0.45 g (0.5 wt %) of bismuth neodecanoate catalyst was added. After stirring the mixture for an additional 5 minutes, stirring was stopped and the reactor was placed in an oil bath and heated to 60° C. The mixture was heated for 24 hours during which time no elastomeric gel was formed.

TABLE 1

Experimental parameters and characterization data for the formation of rubbers described in Examples 1-5.

| Material | Example 1 Rubber wt % | Mass | Example 2 Rubber wt % | Mass | Example 3 Rubber wt % | Mass | Example 4 Rubber Wt % | Mass | Example 5 Rubber Wt % | Mass |
|---|---|---|---|---|---|---|---|---|---|---|
| DAPD | 12.5 | 11.25 | 18.94 | 17.05 | 7.58 | 6.82 | 12.5 | 11.25 | 12.5 | 11.25 |
| PDT | 3.5 | 3.15 | 5.3 | 4.77 | 2.12 | 1.91 | 3.5 | 3.15 | 3.5 | 3.15 |
| Bismuth neodecanoate | 0.5 | 0.45 | 0.76 | 0.68 | 0.3 | 0.27 | 0.5 | 0.45 | 0.5 | 0.45 |
| Coco-Caprylate/Caprate | 20.9 | 18.81 | 18.78 | 16.9 | 22.52 | 20.27 | 0 | 0 | 83.5 | 75.1 |
| Glyceryl Triheptanoate | 62.6 | 56.34 | 56.22 | 50.6 | 67.48 | 60.73 | 83.5 | 75.15 | 0 | 0 |
| Total | 100 | 90 | 100 | 90 | 100 | 90 | 100 | 90 | 100 | 90 |
| Appearance | Moderately firm, hazy rubber | | Firm, hazy rubber | | Soft, hazy rubber | | Moderately firm, clear rubber | | Clear solution, no gelation | |
| Texture Analyzer, Force, (Grams (g)) | 1269.8 | | 3234.2 | | 230.82 | | 1176.9 | | No Rubber Formed | |

TABLE 1-continued

Experimental parameters and characterization data for the formation of rubbers described in Examples 1-5.

| Material | Example 1 Rubber wt % | Mass | Example 2 Rubber wt % | Mass | Example 3 Rubber wt % | Mass | Example 4 Rubber Wt % | Mass | Example 5 Rubber Wt % | Mass |
|---|---|---|---|---|---|---|---|---|---|---|
| Texture Analyzer, Force, (Newtons (N)) | 12.45 | | 31.72 | | 2.26 | | 11.54 | | No Rubber Formed | |
| Resilience, % | 96.4 | | 95.3 | | 82.3 | | 96.3 | | No Rubber Formed | |

Example 6: Process for Preparing an Elastomer Gel Containing a Volatile Cosmetic Emollient A mixing vessel is charged with 100 g of Example 1 rubber and 11.1 g of glyceryl triheptanoate. The mixture is milled by applying high shear mixing to generate a viscous paste to generate a viscous paste containing generally sub-100 micron particles. The mixture is further diluted with 12.3 g of glyceryl triheptanoate to form a soft, concentrated pre-elastomer by high shear mixing which is then dispersed through a high shear mill to render the polyurethane particles to less than about 60 microns. The particle concentrate is further diluted with mixing by adding 18 g of C9-C12 alkanes (Vegelight 1214, Grant Industries, USA) to produce a smooth cosmetic elastomer with a slightly volatile texture profile and a viscosity of 102,440 cP (Brookfield DV-I+, Spindle TD, 1.5 RPM). This elastomer gel will be commercially available as a part of the Gransense™ product line from Grant Industries (Elmwood Park, N.J., USA).

Example 7. Process for Preparing an Elastomer Gel Containing a Non-Volatile Cosmetic Emollient A mixing vessel is charged with 100 g of/Example 1 rubber and 11.1 g of glyceryl triheptanoate. The mixture is milled as described in the preceding example. The mixture is diluted with 12.3 g of glyceryl triheptanoate to form a soft, concentrated pre-elastomer by high shear mixing to reduce the polyurethane particles to less than about 60 microns. The particle concentrate is further diluted with mixing by adding 30 g of glyceryl triheptanoate to produce a bouncy cosmetic elastomer with a moisturizing skin feel and a viscosity of 416,667 cP (Brookfield DV-I+, Spindle TE, 0.6 RPM). This elastomer gel will be commercially available as a part of the Gransense™ product line from Grant Industries (Elmwood Park, N.J., USA).

Example 8. Process for preparing a low-viscosity elastomer containing a non-volatile cosmetic emollient A mixing vessel is charged with 100 g of/Example 1 rubber and 11.1 g of glyceryl triheptanoate. The mixture is milled as described in the preceding example. The mixture is diluted with 12.3 g of glyceryl triheptanoate to form a soft, concentrated pre-elastomer by high shear mixing to reduce the polyurethane particles to less than about 60 microns. The particle concentrate is further diluted with mixing by adding 58.4 g of glyceryl triheptanoate to produce a pourable cosmetic elastomer with a moisturizing and velvety skin feel and a viscosity of 37,500 cP (Brookfield DV-I+, Spindle TC, 3.0RPM). This elastomer gel will be commercially available as a part of the Gransense™ product line from Grant Industries (Elmwood Park, N.J., USA).

As outlined in the description of the invention, the formation of a polyurethane rubber is not limited to the components provided in Examples 1-5. For Example 9, the prepolymer was a copolymer of C18 unsaturated fatty acid dimers and bio-derived 1,4-butanediol (DABD) with a hydroxyl value within the range of 80-100 mg KOH/g. For Example 10, the cosmetic emollient was a mixture of isododecane and coco-caprylate/caprate. For Example 11, the selected pre-polymer was castor oil (CO). For Example 12, the catalyst selected was zinc neodecanoate. For Example 13, the polyisocyanate used was hexamethylene diisocyanate trimer (HDT). Rubbers were prepared from the reaction equivalents provided in Table 2 by following the protocol described for Examples 1-5.

TABLE 2

Experimental parameters and characterization data for the formation of rubbers described in Examples 9-13.

| Material | | Example 9 wt % | Example 10 wt % | Example 11 wt % | Example 12 wt % | Example 13 wt % |
|---|---|---|---|---|---|---|
| Pre-Polymer | DAPD | 0 | 12.5 | 0 | 11.25 | 12.35 |
| | DABD | 11.88 | 0 | 0 | 0 | 0 |
| | CO | 0 | 0 | 10.8 | 0 | 0 |
| Polyisocyanate | PDT | 4.04 | 3.5 | 7 | 3.15 | 0 |
| | HDT | 0 | 0 | 0 | 0 | 3.6 |
| Catalyst | Bismuth Neodecanoate | 0.58 | 0.5 | 0.5 | 0 | 0.52 |
| | Zinc Neodecanoate | 0 | 0 | 0 | 1.8 | 0 |

TABLE 2-continued

Experimental parameters and characterization data for the formation of rubbers described in Examples 9-13.

| | Material | Example 9 wt % | Example 10 wt % | Example 11 wt % | Example 12 wt % | Example 13 wt % |
|---|---|---|---|---|---|---|
| Emollient | Coco-Caprylate/Caprate | 62.62 | 41.75 | 0 | 61.48 | 62.63 |
| | Glyceryl Triheptanoate | 20.88 | 0 | 81.7 | 20.52 | 20.86 |
| | Isododecane | 0 | 41.75 | 0 | 0 | 0 |
| Total | | 100 | 100 | 100 | 100 | 100 |
| Appearance | | Moderately firm hazy rubber | Soft hazy rubber | Firm clear rubber | Hazy soft rubber | Moderately firm hazy rubber |
| Texture Analyzer, Force, (Grams (g)) | | 830.44 | 226.59 | 2993.06 | 300.81 | 926.33 |
| Texture Analyzer, Force, (Newtons, (N)) | | 8.14 | 2.22 | 29.35 | 2.95 | 9.08 |

Example 14. Process for Preparing an Elastomer Gel Containing a Personal Care Active A mixing vessel equipped with side-sweep is charged with 90 g of Example 6 and stirred at 120 RPM. To this is added 20 g of finely milled ascorbic acid in portions over 1 hour. The mixture is stirred until homogenous to generate a viscous, opaque white paste.

Example 15. SPF-50 Sunscreen

To prepare an SPF-50 sunscreen, the ingredients in Phase A, including the elastomer from Example 6, were combined in the main kettle with homogenizer and mixed until uniform. Then Phase B was added to the main kettle while mixing with a side sweep agitator blade until uniform. The SPF was measured in vitro based on the usage recommendations for zinc oxide and titanium dioxide products from Grant Industries.

Example 16. W/O Emulsion Cream

Incorporation of the elastomer from this invention allows for the stabilization of a W/O emulsion cream with a viscosity ranging between 5,000-50,000 cPs. The presence of the invented elastomer provided higher compatibility with the polar oil phase of this formula as well as the natural polyglyceryl-based emulsifier while achieving the desirable cushion/cloud-like feel that is usually only attainable with silicone elastomer formulations. There is a market demand for higher natural content in cosmetic formulas with formulators opting for naturally derived surfactants, emollients, and thickening aids. As demonstrated by this formulation, the elastomer of this invention provides broader formulating possibilities in the natural and bio-derived formulation landscapes and will also enable the development of products with desirable textural and performance profiles.

To prepare the W/O emulsion cream containing the Gransense™ elastomer from Example 6, first combine the Phase A ingredients from Table 4 in a vessel and mix with a homogenizer at room temperature until a uniform consis-

TABLE 3

Formula for the preparation of an SPF-50 sunscreen containing the Gransense ™ elastomer gel from Example 6.

| Phase | Ingredient Trade Name | Description (Manufacturer) | Weight % |
|---|---|---|---|
| A | Purolan IDD | Isododecane (Lanxess) | 13.50 |
| | Cetiol LC | Coco-caprylate/caprate (BASF) | 2.00 |
| | Bentone Gel ISD V | Isododecane & Disteardimonium Hectorite & Propylene carbonate (Elementis) | 12.50 |
| | Granpowder EDC-600 | Divinyldimethicone/Dimethicone/phenylsilsesquioxa ne crosspolymer (Grant Industries) | 4.00 |
| | UV Cut TIO2-55-CG | Titanium dioxide & caprylic/capric triglyceride & stearic acid & alumina & polyhydroxystearic acid (Grant Industries) | 20.00 |
| | UV Cut ZNO-68-CG | Zinc oxide & caprylic/capric triglyceride & polyhydroxystearic acid (Grant Industries) | 25.00 |
| | Granresin PMSQ-ID | Polymethylsilsesquioxane & Isododecane (Grant Industries) | 5.00 |
| | EXAMPLE 6 | Gransense ™ Elastomer Gel | 15.00 |
| | Pelemol PHS-8 | Polyhydroxystearic acid (Phoenix Chemical) | 2.00 |
| B | Aerosil 200 | Silica (Evonik) | 1.00 |
| | Formula Total | | 100.00 | tency is obtained. In a side vessel, combine the Phase B ingredients. Add the Phase B ingredients to Phase A while homogenizing and mix until uniform.

TABLE 4

Formula for the preparation of a W/O emulsion cream containing the Gransense™ elastomer gel from Example 6.

| Phase | Ingredient Trade name | Description (Manufacturer) | Weight % |
|---|---|---|---|
| A | Cetiol LC | Coco-Caprylate/caprate (BASF) | 12.40 |
|  | Naturesoft 800 | Cellulose (Micropowders Inc) | 2.00 |
|  | Zea Mays (Corn) Starch | Agenaflo 9050 (Agrana) | 2.00 |
|  | EXAMPLE 6 | Gransense™ Elastomer gel | 15.00 |
|  | Gransurf PG-14 | Polyglyceryl-6 polyricinoleate & polyglyceryl-10 dioleate (Grant Industries) | 7.00 |
|  | Aerosil 200 | Silica (Evonik) | 0.20 |
| B | Deionized Water |  | 50.20 |
|  | Glycerin | Glycerin | 5.00 |
|  | Butylene Glycol | Butylene Glycol | 3.00 |
|  | Sodium Chloride | Sodium Chloride | 0.70 |
|  | Nipaguard SCM | Methylisothiazolinone & propylene glycol & sorbitan caprylate | 1.00 |
|  |  | Formula Total | 100.00 |

Example 17. Cream-to-Powder Foundation

Incorporation of the elastomer from this invention allows for the stabilization of a W/O emulsion cream with a viscosity ranging between 500,000-1,000,000 cPs. Presence of the invented elastomer from Example 6 allowed the use and stabilization of Amino Acid treated inorganic pigments. Amino acid treated pigments are commonly used in color cosmetics however a high percentage and myriad combinations of difference emulsifiers and wetting agents are generally required for their stabilization. Combination of the invented elastomer gel from Example 6 with natural polyglyceryl and phospholipid-based emulsifiers in the presence of a polar oil phase allowed a stable W/O, while achieving known silicone elastomer cushion/cloud-like feel. To prepare the cream-to-powder foundation containing the Gransense™ elastomer from Example 6, combine ingredients from Phase A listed in Table 5 in the main vessel and mix with a homogenizer until uniform. In a separate container, combine Phase B ingredients and micro-pulverize until the color is fully blended and uniform. Add Phase B to Phase A while homogenizing until uniform. In a side vessel, combine Phase C ingredients and mix with a homogenizer. Add Phase C to Phase AB while homogenizing until a uniform foundation cream is obtained.

TABLE 5

Formula for the preparation of a cream-to-powder foundation containing the Gransense™ elastomer gel from Example 6.

| Phase | Ingredient Trade Name | Description (Manufacturer) | Weight % |
|---|---|---|---|
| A | Cetiol LC | Coco-caprylate/caprate (BASF) | 10.00 |
|  | Vegelight 1214 | Coconut alkanes & coco-caprylate/caprate (Grant Industries) | 1.00 |
|  | EXAMPLE 6 | Gransense™ Elastomer Gel | 15.00 |
|  | Gransurf PG-14 | Polyglyceryl-6 polyricinoleate & polyglyceryl-10 dioleate (Grant Industries) | 8.00 |
|  | Lecithin | Lecithin | 1.50 |
| B | NAI-TR-10 | Titanium dioxide & disodium stearoyl glutamate & aluminum hydroxides (Miyoshi) | 7.2 |
|  | NAID-Y-77492 | Iron oxides (CI 77492) & disodium stearoyl glutamate & aluminum hydroxides (Miyoshi America) | 2.10 |
|  | NAID-R-77491 | Iron oxides (CI 77492) & disodium stearoyl glutamate & aluminum hydroxides (Miyoshi America) | 0.47 |
|  | NAID-B-77499 | Iron oxides (CI 77499) & disodium stearoyl glutamate & aluminum hydroxides (Miyoshi America) | 0.19 |
|  | Sericite DNN | Mica (Ikeda) | 6.00 |
|  | Silica | Silica | 0.70 |
| C | Deionized Water |  | 34.87 |
|  | Bentone Hydroclay 2000 | Hectorite (Elementis) | 2.00 |
|  | Glycerin | Glycerin | 5.00 |
|  | Butylene Glycol | Butylene Glycol | 1.00 |
|  | Solagum AX | Acacia Senegal gum & xanthan gum (Seppic) | 0.07 |
|  | Lexgard Natural | Glyceryl caprylate & glyceryl undecylenate (Inolex) | 1.00 |
|  | Sodium chloride | Sodium chloride | 0.70 |
|  |  | Formula total | 100.00 |

Example 18. Luminous Lipstick

The invented elastomer is ideal for lip-care applications due to its good compatibility with common cosmetic waxes and pigments. When added to a lip care formulation, the invented elastomer provides moisturization, cushiony feel, and improved compatibility between the varyingly polar and apolar ingredients.

To prepare a luminous lipstick containing the Gransense™ Elastomer from Example 6, the ingredients from Table 6 were weighed into the main kettle, which was equipped with a 3-prong blade. The vessel was heated to 90-95° C. and mixed until uniform. The lipstick is poured into a lipstick applicator package at 75-80° C.

TABLE 6

Formula for the preparation of a luminous lipstick containing the Gransense ™ elastomer gel from Example 6.

| Phase | Ingredient Trade Name | Description (Manufacturer) | Weight % |
|---|---|---|---|
| A | Refined Candelilla Wax MD-21 | *Euphoria Cerifera* (Candelilla) Wax (Ikeda) | 13 |
|  | Carnauba Wax | *Copernica Cerifera* (Carnauba) Wax (Koster Keunen) | 3 |
|  | NF Yellow Beeswax 423 G | Beeswax (Koster Keunen) | 2 |
|  | Rita SAO | *Prunus Amygdalus Dulcis* (Sweet Almond) Oil (Rita Corporation) | 18 |
|  | Eutanol G | Octyldodecanol (BASF) | 5 |
|  | Coconut Oil | *Cocos Nucifera* (Coconut) oil (Jeen) | 1.5 |
|  | EXAMPLE 6 | Gransense ™ Elastomer gel (Grant Industries) | 15 |
|  | D&C Red No. 7, 40% in Castor Oil | *Ricinus Communis* Seed Oil & Red 7 (Miyoshi) | 30 |
|  | TIO2, 50% in Castor Oil | Titanium dioxide (and) Castor Oil (Miyoshi) | 8 |
|  | Aerosil 200 | Silica (Evonik) | 0.4 |
|  | Sucralose | Sucralose | 0.1 |
|  | Covi-OX T-90 EU C | Tocopherol (BASF) | 1 |
|  | Kester Wax K-60P | Polyhydroxystearic Acid (Koster Keunen) | 3 |
|  |  | Formula Total | 100 |

Example 19. Repairing Shampoo

To prepare a repairing shampoo containing the Gransense™ Elastomer from Example 8, the ingredients from Table 7 were weighed into the main kettle and homogenized. Phase B was sprinkled into Phase A with mixing. Phase C was weighed in a side kettle and heated to a proper temperature whereupon it was added to Phase AB and mixed for 10-15 minutes. Then Phase D was added and mixed for 5-10 minutes. To finish, Phase E was added and mixed into the formula.

TABLE 7

Formula for the preparation of a repairing shampoo containing the Gransense ™ elastomer gel from Example 8.

| Phase | Ingredient Trade Name | Description (Manufacturer) | Weight % |
|---|---|---|---|
| A | Deionized Water | Water | 47.7 |
|  | Carbopol Aqua SF-1 Polymer | Acrylates Copolymer (Lubrizol) | 5 |
| B | Jaguar C-14S | Guar Hydroxypropyltrimonium Chloride (Solvay) | 0.3 |
| C | Iselux Ultra Mild | Water (and) Sodium Methyl Isethionate (and) Cocamidopropyl Betaine (and) Sodium Methyl Oleyl Taurate (and) Lauryl Glucoside (and) Coco-Glucoside (Innospec) | 37 |
|  | Chembetaine C | Cocamidopropyl Betaine (Lubrizol) | 2 |
|  | Jeemide HCA-RC3 | Cocamide DEA (Jeen) | 3 |

TABLE 7-continued

Formula for the preparation of a repairing shampoo containing the Gransense ™ elastomer gel from Example 8.

| Phase | Ingredient Trade Name | Description (Manufacturer) | Weight % |
|---|---|---|---|
| D | EXAMPLE 8 | Gransense ™ Elastomer Gel (Grant Industries) | 2 |
|  | Euperlan PK 771 | Glycol Distearate (and) Sodium Laureth Sulfate (and) Cocamide MEA (and) Laureth-10 (BASF) | 3 |
| E | Lexguard Natural | Glyceryl Caprylate (and) Glyceryl Undecylenate (Inolex) | 1 |
|  | Orchidia Gras Ocean Waves Fragrance ORC1500049 | Fragrance | 0.5 |
|  |  | Formula Total | 100 |

Example 20. Anhydrous Formulation

The invented elastomer gel can be used in anhydrous cosmetic and personal care formulations when advantageous. To prepare an anhydrous formula containing the Gransense™ elastomer gel from Example 6, the ingredients from Table 8 were combined together by mixing until homogenous. The anhydrous formulation described below can serve as a carrier for cosmetic active ingredients in other anhydrous formulations.

TABLE 8

Formula for the preparation of an anhydrous formula containing the Gransense ™ elastomer gel from Example 6.

| Phase | Ingredient Trade Name | Description (Manufacturer) | Weight % |
|---|---|---|---|
| A | EXAMPLE 6 | Gransense ™ Elastomer gel | 70.0 |
|  | Cetiol B | Dibutyl Adipate (BASF) | 30.0 |
|  |  | Formula Total | 100.0 |

Compatibility with Common Personal Care Ingredients

To demonstrate the unique compatibility of the polyurethane elastomer of this invention with common personal care ingredients and emollients, the elastomer from Example 6 was mixed with the selected personal care ingredients in ratios of 1:9, 1:1, and 9:1. When a solid or wax is used, the elastomer and wax were heated to the melting point of the wax and then combined and allowed to cool. The mixtures are evaluated and ranked according to the keys in the footnote of the following table. A commercial silicone elastomer blend from Grant Industries was used as reference. The results are shown below. Compared to a conventional silicone elastomer gel, the polyurethane elastomer gel of this invention can be dispersed in cosmetic esters as well as common cosmetic waxes. Interestingly, the polyurethane elastomer gel is more compatible with sunscreen actives than the silicone elastomer.

TABLE 9

Summary of compatibility results of various cosmetic raw materials with Gransense ™ elastomer gel from Example 6 as compared to a common silicone elastomer.

| Raw Material | Gransense ™ Elastomer (Example 6) | | | Gransil DMCM-5 | | |
|---|---|---|---|---|---|---|
|  | 9:1 | 1:1 | 1:9 | 9:1 | 1:1 | 1:9 |
| Dimethicone, 5 cst | I | I | OD | T | HD | C/T |
| Isododecane | I | I | OD | C | C | C |
| Ethylhexyl methoxycinnamate | T | HD | OD | I | I | OD |
| Castor Oil | HD | HD | HD | I | I | OD |
| C12-15 Alkyl Benzoate | T | OD | OD | I | OD | C |
| Coco-Caprylate/Caprate | HD | HD | HD | I | OD | C |
| Beeswax* | D* | C* | C* | I* | C* | C* |
| Carnauba Wax* | D* | D* | C* | I* | C* | I* |
| Avobenzone* | D* | D* | C* | I* | I* | I* |

C = clear,
T = translucent,
HD = Hazy/Dispersible,
OD = Opaque/Dispersible,
I = Incompatible,
*= wax (heated to melting point then mixed),
C* = Compatible (homogenous),
D* = dispersible (some crystallization),
I* = incompatible (separation)

Evaluation of Rubber Hardness

Elastomeric rubbers and the gelled compositions prepared from the rubbers can be characterized by their hardness or firmness. The Gelatin Manufacturers Institute of America employs equipment such as a "texture analyzer" (Model TA.XT Plus, Stable Micro Systems Inc., Godalming, England) to quantify the hardness or firmness of materials with similar properties to the compositions of rubbers and gels described in this invention. By using a texture analyzer, the surface of the rubbers and gels are subjected to compression by a probe with a 5.0 kg weight as the load cell, at a determined speed of 1.0 mm/s, and to a programmed depth of 10 mm into the rubber or gel, followed by retreat at the same speed. The resistance force detected by the probe of the Texture Analyzer during the compression of the gel or rubber defines the "hardness" as taught by Lin et al. (U.S. Pat. No. 8,222,363 B2). The hardness value measured by the Texture Analyzer is recorded by Gram (g) force and can be converted to Newton (N) by dividing by 101.97.

In this invention, the hardness of the rubber, measured by the Texture Analyzer as the force in grams applied by the rubber when compressed, is a determining factor in the successful formation of elastomeric gels from the respective elastomeric rubber precursor. By varying the concentration of the polyurethane-forming components of rubber composition (i.e. pre-polymer and polyisocyanate moieties), rubbers of varying hardnesses were formed. Additionally, the identity of the cosmetic emollient chosen as a matrix had an effect on the rubber hardness. It was determined that suitably hard gels were formed when mixtures of the required components were combined to form a gel with a minimum hardness of 200.0 g, preferably 500.0 g, to maximally 4000 g, as determined by Texture analysis prior to milling or diluting the formed rubber When the rubber hardness was below 200.0 g, or above 4000 g hardness, a suitable elastomeric rubber could not be yielded through the above described milling procedures.

An additional parameter provided by the texture analyzer was the resilience of the rubber. We defined the resilience as the area of the force curve after release of compression (Force-Time area 2-3), divided by the area of the force curve during the compression (Force-Time area 1-2), multiplied by 100%. A resilience value of 100% would represent an idealized elastic material. Through experimentation, it was determined that a suitable polyurethane rubber, as described by this invention, requires a resilience value of at least 70%, preferably at least 90%.

Example 21—Testing the Ultimate Biodegradability/Inherent Biodegradability of the Gransense™ Elastomer Gel The elastomer gel of Example 6 was submitted for biodegradation testing in accordance with OECD 301 B: $CO_2$ Evolution (Modified Sturm Test) at Situ Biosciences (Wheeling, Ill.).

Figure 1:
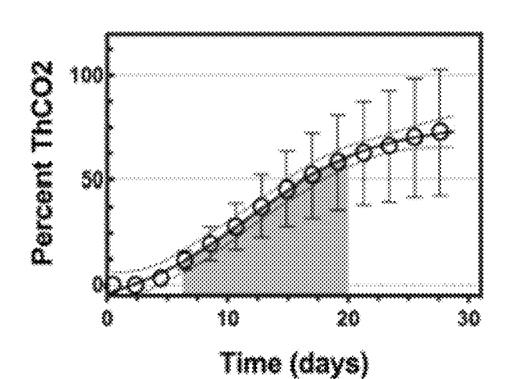
FIG. 1 is biodegradation graph corresponding to Example 21.

A sample was submitted, and the results data and graph were analyzed by curve fit to establish a plateau for the rate of biodegradation. Referring now to FIG. 1, the OECD 301B-Biodegradation graph shows the test chamber carbon dioxide (CO2) measurements as the percent of theoretical maximum (% ThCO2). Curve fit is applied to calculate the predicted fit (solid curve line). The shading below the curve fit applies to the biodegradation requirement (10 to 60% ThCO2) for the determination of Biodegradability and shows that the required degradation amount has been met. See WO 2014/167518A, the contents of which are incorporated herein by reference.

In conclusion, the sample achieved the requirements for Ultimate Degradation/Inherent Biodegradation by exceeding the 60% threshold before the end of the 28-day test time frame.

Example 22: Testing for the % Bio-Based Carbon Content of the Gransense™ Elastomer Gel The elastomer gel of Example 6 was submitted for % Biobased Carbon in accordance with ASTM D6866-18 Method B using Radiocarbon Isotope Analysis at Beta Analytic Inc (Miami, Fla.). A naturally occurring isotope of carbon that is radioactive and decays in such a way that there is none left after about 45,000 years following the death of a plant or animal. Interpretation and application of the results is straightforward. A value of 100% biobased or biogenic carbon would indicate that 100% of the carbon came from plants or animal by-products (biomass) living in the natural environment and a value of 0% would mean that all of the carbon was derived from petrochemicals, coal, and other fossil sources. A value between 0-100% would indicate a mixture. The higher the value, the greater the proportion of naturally sourced components in the material.

A sample was submitted, and the results data concluded that the sample contained 100% Biobased Carbon Content (as a fraction of total organic carbon).

We claim:

1. A non-aqueous gel composition comprising a mixture of a cross-linked polyurethane elastomer rubber composition, comprising (a) a cross-linked polyurethane elastomer rubber; (b) a cosmetic emollient and (c) a urethanation catalyst, wherein the cosmetic emollient forms a solvent matrix substantially surrounding the cross-linked polyurethane elastomer rubber in micronized form and at least one cosmetic emollient.

2. The non-aqueous gel composition of claim 1, wherein the amount of the micronized cross-linked polyurethane elastomer rubber composition is from about 30 to about 5 weight %.

3. The non-aqueous gel composition of claim 1, wherein the amount of the cosmetic emollient is from about 70 to about 95 weight %.

4. The non-aqueous gel composition of claim 1, further comprising a secondary solvent.

5. The non-aqueous gel composition of claim 4, wherein the secondary solvent is selected from the group consisting of triheptanoin; undecane; tridecane; or wherein the secondary solvents are naturally derived alkanes or naturally derived esters.

6. The non-aqueous gel composition of claim 1, further comprising an active composition, optionally selected from the group consisting of selected from vitamins, sunscreens, plant extracts, fragrances and mixtures thereof.

7. The non-aqueous gel composition of claim 1, further comprising a member of the group consisting of fragrances, colorants, preservatives, active compositions, and mixtures thereof.

8. The non-aqueous gel composition of claim 1, wherein the micronized cross-linked polyurethane elastomer rubber composition has a cross-sectional diameter of from about 1 to about 61 microns.

9. The non-aqueous gel composition of claim 1, having a viscosity ranging from about 15,000 cP to about 1,000,000 cP.

* * * * *